Figure 1:
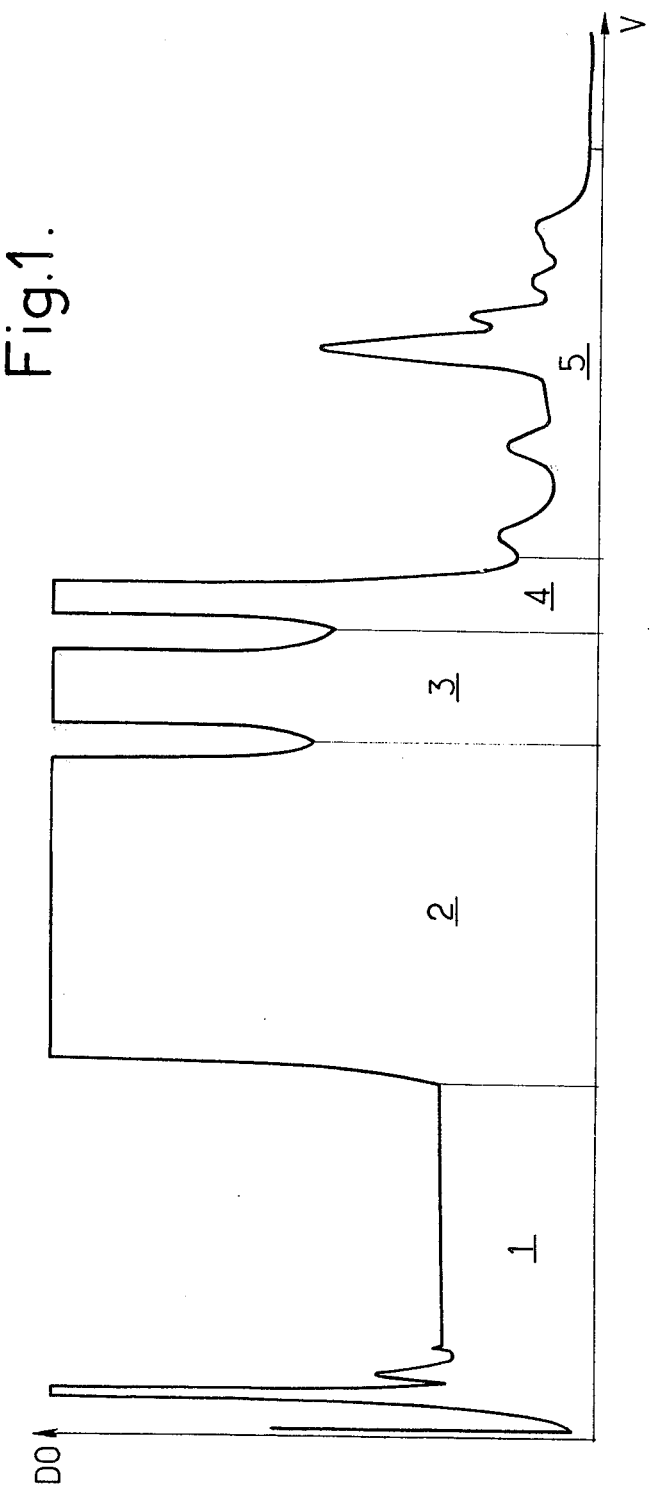

United States Patent [19]

Lormeau et al.

[11] 4,401,758

[45] Aug. 30, 1983

[54] PROCESS FOR MAKING OLIGOSACCHARIDES HAVING ANTI-XA ACTIVITY AND THE RESULTING OLIGOSACCHARIDES

[75] Inventors: Jean-Claude Lormeau, Maromme La Maine; Jean Choay; Maurice Petitou, both of Paris, all of France

[73] Assignee: Choay S.A., Paris, France

[21] Appl. No.: 194,544

[22] Filed: Oct. 6, 1980

Related U.S. Application Data

[63] Continuation-in-part of Ser. No. 91,164, Nov. 5, 1979, abandoned.

[30] Foreign Application Priority Data

| Oct. 5, 1979 | [GB] | United Kingdom | 7934673 |
| Jan. 7, 1980 | [GB] | United Kingdom | 8000443 |
| Jul. 2, 1980 | [GB] | United Kingdom | 8021749 |
| Jul. 2, 1980 | [GB] | United Kingdom | 8021750 |
| Sep. 15, 1980 | [GB] | United Kingdom | 8029697 |

[51] Int. Cl.³ .................... C12P 19/26; C08B 37/10; C07H 5/06
[52] U.S. Cl. .................................. 435/84; 424/180; 424/183; 536/18.7; 536/21; 536/55.3
[58] Field of Search ............... 536/1, 18, 21, 18.7, 536/55.3; 424/183; 435/84

[56] References Cited

U.S. PATENT DOCUMENTS

| 3,506,642 | 4/1970 | Koh et al. | 536/21 |
| 3,985,871 | 10/1976 | Butti et al. | 424/183 |
| 4,122,250 | 10/1978 | Schmer | 536/21 |
| 4,175,182 | 11/1979 | Schmer | 536/21 |
| 4,213,962 | 7/1980 | Miura et al. | 424/183 |
| 4,281,108 | 7/1981 | Fussi | 536/21 |

FOREIGN PATENT DOCUMENTS

2002406  2/1979  United Kingdom .................. 536/21

*Primary Examiner*—Johnnie R. Brown
*Attorney, Agent, or Firm*—Weiser, Stapler & Spivak

[57] ABSTRACT

Oligosaccharides obtainable from heparin including heparinic constituents of molecular weights ranging from 2000 to 50,000. Said fractions have a Yin-Wessler titer and a USP titer in a ratio of at least 30.

They consist of chains substituted by no more than 8 saccharidic moities. They possess a strong antithrombotic activity and are then useful as antithrombotic drugs.

15 Claims, 6 Drawing Figures

PROCESS FOR MAKING OLIGOSACCHARIDES HAVING ANTI-XA ACTIVITY AND THE RESULTING OLIGOSACCHARIDES

This application is a continuation-in-part of patent application Ser. No. 091,164, filed Nov. 5, 1979, which application has been abandoned in favor of pending application Ser. No. 204,505 filed Nov. 6, 1980.

BACKGROUND OF THE INVENTION

The invention relates to oligosaccharidic fractions and to oligosaccharides having biological properties, particularly the ability of more specifically controlling some steps of the blood coagulation.

The invention also relates to processes for obtaining said products and to the use of said products as active principles in drugs.

The invention relates more particularly to oligosaccharides having a highly selective activity against activated factor X or factor Xa of blood i.e. a strong antithrombotic activity while avoiding the risk of hemorrhage for the patient, as well as to oligosaccharidic fractions containing such oligosaccharides (the term "oligosaccharidic fractions" is used in the specification and the claims to designate a relatively homogeneous mixture of oligosaccharidic fragments or chains having a variable number of saccharidic moieties).

The inventors have been led to investigate the biologically active oligosaccharidic fractions and the oligosaccharides themselves, such as obtained from heparin.

It will be noted that term heparin is used in the specification and the claims in its broadest sense, in order to designate either a commercial heparin of pharmaceutical grade or a crude heparin such as obtained by extraction from biological material, particularly from mammalian tissue.

It is admitted that heparin is an heterogeneous polysaccharide with respect to the composition of its oligosaccharidic chains as well as to the molecular weight thereof.

It is generally considered that heparin mainly contains 2-0-sulfate-L-iduronic acid and N-sulfate-D glucosamine (6-0-sulfated or not) and to a lesser extent D-glucuronic acid, L-iduronic acid and N-acetyl-D-glucosamine (6-0-sulfated or not) moieties.

It is also known that heparin produces its anticoagulant activity by potentiating the inhibitory effect of antithrombin III (or ATIII) which is a plasma protein against the successive enzymatic reactions of the coagulation cascades. As heparin is able to simultaneously depress a large number of the coagulation factors participating in the creation and the upkeeping of different forms of hypercoagulability, its activity does not appear specific but general.

Although this anticoagulant activity turns out to be valuable, the re-equilibration of the coagulation-fibrinolysis system with patients under treatment is delicate, due to the global nature of its action. As a result the administration (in order to prevent hypercoagulation risks, for example, the spectre of post-surgical thrombosis) of too high doses of anticoagulant drug or the insufficient selectivity of that drug can be responsible for serious hemorrhages.

SUMMARY OF THE INVENTION

By thoroughly studying various conditions for depolymerizing heparin and the depolymerization mixtures thus obtained, the inventors have been led to notice that under certain conditions, it is possible to obtain valuable antithrombotic oligosaccharides containing mixtures. These oligosaccharides are more satisfactory than heparin with regard to the specificity of their activity. They are more particularly capable of enhancing the specific activity of ATIII with respect to a smaller number of coagulation factors, more especially with respect to factor Xa. More essentially, it has been found that such fractions and oligosaccharides have a low global anticoagulant activity as measured by the USP method and that consequently the ratio of their anti-Xa activity as expressed in Yin-Wessler units and of their USP titer is high, at least 30.

As is well-known, the Yin-Wessler activity is more specifically representative of the capability of the active fractions to potentiate the inhibition of the activated factors Xa of blood by AT III in the corresponding test and the UPS titer is representative of the capability of the active fractions to inhibit the global coagulation of blood or plasma.

The Yin-Wessler titer is measured by the test described by these authors in J. Lab. Clin. Med. 1976,81,298–300, and the U.S.P. titer is measured by the test which is described in the "Pharmacopea of the United States of America", XIX, pp. 229-230 (see also the second supplement U.S.P.—NF, p. 62 and the fourth supplement U.S.P.—NF, p. 90 respectively entitled "Drug Substances" and "Dosage Forms".

Unexpectedly, it has thus been noticed that the desired anti-Xa specific activity was found in the short oligosaccharidic chains, i.e. containing no more than 8 saccharidic moieties, which can be isolated from the depolymerization mixtures by resorting to certain purification steps, carried out under specified conditions.

It will be noted that the terms "saccharidic moiety" is used in the specification and the claims to designate monosaccharides contained in the heparinic chains.

Besides, according to an aspect of great interest, the inventors have found that the anti-Xa activity of said fractions and of the oligosaccharides, such as expressed in Yin-Wessler units, was significant of an antithrombotic activity in vivo.

It is then an object of the invention to provide new oligosaccharides and fractions containing them, having a high anti-Xa activity and a remarkable selectivity in the framework of the successive enzymatic reactions which characterize the coagulation processes. It is another object to provide structural features of these oligosaccharides.

It is a further object of the invention to provide a process of obtaining said fractions which is easy to carry out.

It is still another object of the invention to provide active principles of drugs and the drugs per se, particularly capable of inhibiting the factor Xa with a high degree of selectivity while their activity on global coagulation can be maintained at a very low level. Such drugs are advantageously useful for antithrombotic treatment without haemorrhage risks.

Said oligosaccharidic fractions are of the type obtainable by a process which comprises the steps of contacting heparin (or heparinic fractions) possessing anticoagulant activity and having chains with molecular weights ranging from about 2000 to about 50,000, with an agent capable of depolymerizing or fragmenting the heparinic chains, the conditions used for carrying out that step being adjusted so as to obtain a depolymerization mixture which contains oligosaccharidic fragments or chains, constituted by no more than 8 moieties yet having an anti-Xa Yin-Wessler activity and including a sequence consisting of less than 8 moieties, which sequence is responsible, to a large extent, for the specific anti-Xa activity of the products;

treating the depolymerization mixture to separate at least the major part of the above defined oligosaccharidic chains, said treatment advantageously comprising (a) the contact of the depolymerization mixture with ATIII for selecting at least the major part, advantageously practically the totality of the oligosaccharides possessing a sequence having the specific structure necessary to recognize and bind ATIII, (b) the elimination of the unselected products, (c) the recovery of the selected products. Said oligosaccharides can be characterized by the fact they possess a specific structure capable of binding ATIII. They have an anti-Xa activity higher than heparin and a very low global anticoagulant activity.

DESCRIPTION OF THE INVENTION

The products having an ATIII affinity as recovered from the above mentioned process, are submitted to one or several steps in order to selectively separate the above-defined oligosaccharides having short chains.

Said separation is advantageously obtained by fractionating the mixture of the eluted products having ATIII affinity, according to their molecular weight and/or their ionic density, and recovering the desired fractions.

Alternatively, the fractionation can be carried out directly on the depolymerization mixture. At that stage, the fractions comprising short oligosaccharidic chains, advantageously the oligosaccharides per se, can be isolated. The fractions, optionally the oligosaccharides, with a high ATIII affinity are subsequently separated by resorting to a step comprising contacting said fractions as above mentioned with ATIII.

The oligosaccharidic fractions of the invention are of the type of those obtained by resorting to the various steps defined above. They are characterized by the fact that they are free of oligosaccharides comprising more than 8 saccharidic moieties and that they consist of oligosaccharides having no more than 8 saccharidic moieties containing a sequence comprising less than 8 saccharidic moieties, responsible for their anti-Xa activity at least to a major extent.

According to an embodiment, the fractions of the invention are of the type obtainable by a process wherein the heparinic material is depolymerized by a chemical process, in particular with nitrous acid, $HNO_2$, in aqueous medium.

The heparinic chains are thus split between a N-sulfate glucosamine unit and the following uronic acid resulting in chains containing a 2,5-anhydromannose group at their reducing end.

In another embodiment, the depolymerization is carried out under an enzymatic process, advantageously with a highly purified heparinase, more especially a bacterial heparinase.

The enzyme cleaves the haparinic chains between the anomeric carbon of an N-sulfate-glucosamine residue and the following uronic acid unit.

Its action produces a mixture of oligosaccharides (di-,tetra-,hexa-,octasaccharides) with a two fold degree of polymerization and terminated at their non reducing end by an $\alpha,\beta$-unsaturated uronic acid.

The depolymerization with the purified heparinase is advantageously carried out under conditions giving rise to said biologically active oligosaccharides having no more than 8 saccharide moieties and for part of them of 6 or less. Said conditions are such that the limit of the enzymatic reaction is reached. In other words the resulting oligosaccharides are then no longer susceptible to the action of the highly purified heparinase.

The biologically active oligosaccharides then correspond to those separable from said depolymerization mixtures (obtained by chemical or enzymatic way) by adsorption on carrier bound ATIII such as agarose bound ATIII under conditions enabling the products having an ATIII affinity to be fixed or retained on ATIII while those devoid of such an affinity are eliminated for example by rinsing.

This is followed by the elution of the retained or adsorbed products in order to recover them, and by their fractionation for isolating the short chains having an anti-Xa activity.

Optionally, before said separation based on the AT III affinity of the fractions, the depolymerization mixture is submitted to a fractionation as already mentioned, to separate the desired chains. Such a separation is advantageously carried out by gel permeation (gel filtration).

Figure 5:
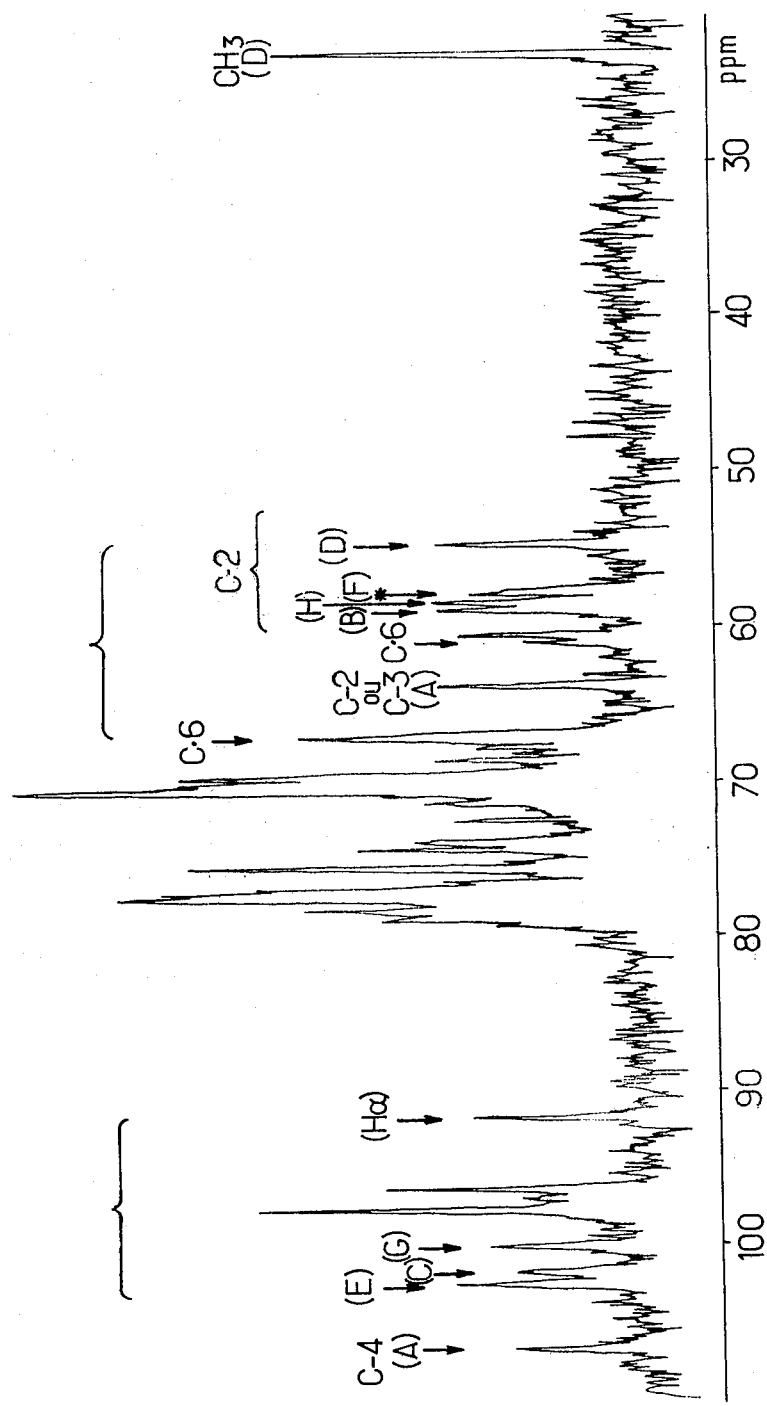
Figure 6:
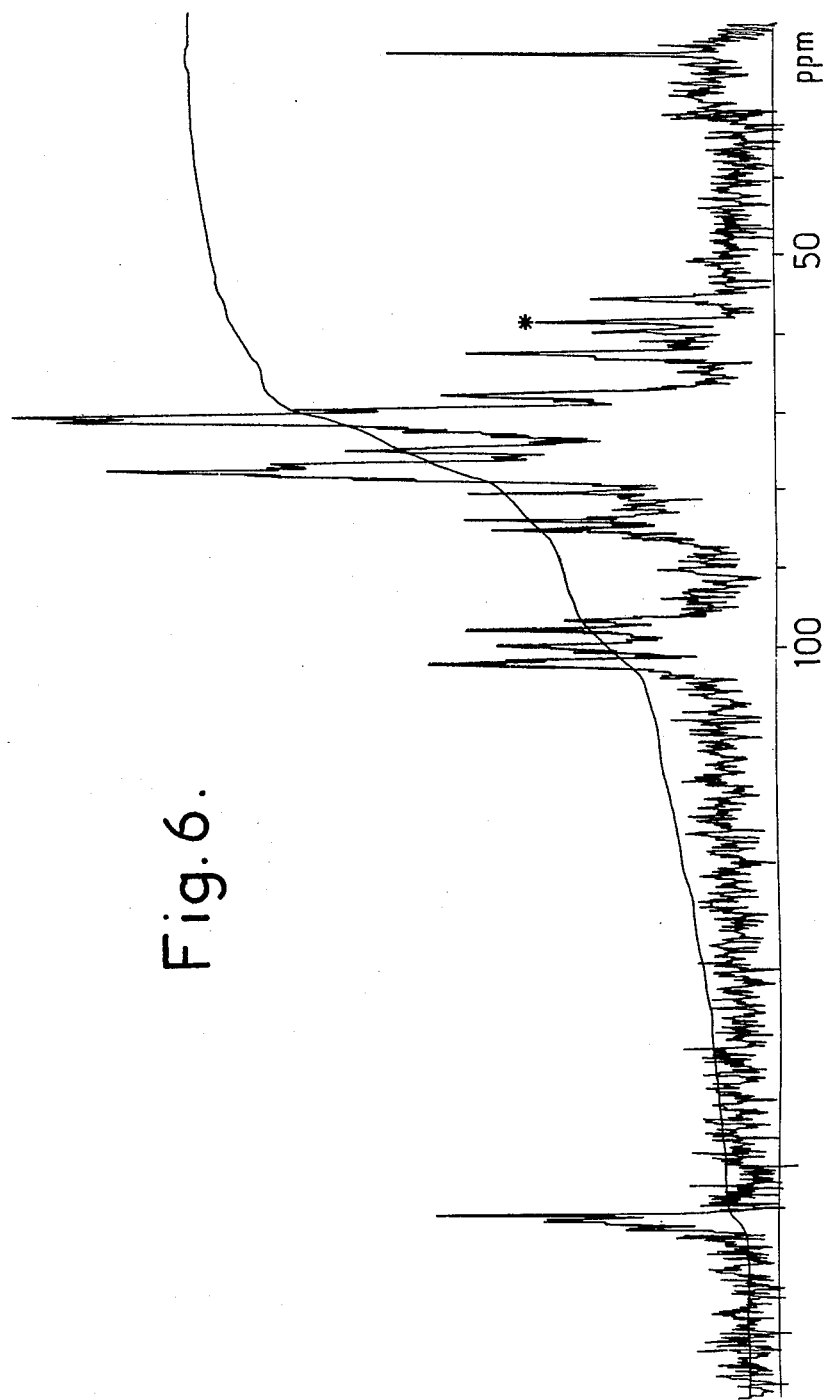

Most of the oligosaccharidic chains such as those above isolated, besides their high AT III affinity and subsequent anti-Xa activity are characterized by NMR spectra comprising among others a characteristic signal in the region of the C-2 of N-sulfate-glucosamine residues (said signal is marked by an asterisk on FIGS. 5 and 6). This signal does not appear with heparin. Very likely it can be related to the presence of a 3-0 substituent and more particularly to a 3-0-sulfate group on a N-sulfate-D-glucosamine moiety.

The oligosaccharides are further characterized by a Yin-Wessler titer and a USP titer which are respectively in a ratio of at least 30, preferably of at least 100.

Preferred oligosaccharidic fractions and oligosaccharides comprise those with an AT III affinity and an anti-Xa (Yin-Wessler) activity which are higher than heparin. Such an anti-Xa activity can be 10 times as high as the one of heparin. Activity higher than 100 iu/mg can be noticed for certain oligosaccharides. Values above 700 iu/mg or of at least 1000 iu/mg, even 1,200, reaching 2,000 iu/mg or more have been observed for other oligosaccharides.

Active oligosaccharides of the invention have a N-sulfated D-glucosamine residue advantageously 3-0 sulfated (designated F in the formula given hereafter).

Other oligosaccharides further comprise a N-acetyl-D-glucosamine residue (D) and/or a D-glucuronic acid residue (E) and/or a 2-0 sulfate-L-iduronic acid residue (G) and/or a N-sulfate-D-glucosamine residue (H).

In other oligosaccharides, the presence of the following saccharidic moieties is observed i.e. a 2-0 sulfate,4,5-unsaturated uronic acid (A) and/or a N-sulfate D-glucosamine unit (B) and/or a L-iduronic acid unit (C).

Preferred oligosaccharides of the invention have a N-sulfate-D-glucosamine residue at their reducing end. This residue is sulfate or not in positions 3 and/or 6.

Some of the oligosaccharides contain all the residues hereabove indicated.

The dosage by colorimetry of N-acetyl-glucosamine units, according to the method of Smith and Gilkerson in Annal. Biochem., 1979,98, p. 478–480, shows then the presence of about one molecule of N-acetylglucosamine by oligosaccharidic chain. Glucosamine dosage before and after acid hydrolysis allows for determination of the respective amount of N-sulfate and N-acetyl-glucosamine.

Some oligosaccharides of the invention appear thus to be characterized by the presence of one N-acetyl-D-glucosamine moiety for the two N-sulfate-glucosamine moieties.

Other oligosaccharides are characterized by the presence of one N-acetyl-D-glucosamine moiety for three N-sulfate-D-glucosamine moieties.

An oligosaccharide of that type is constituted by an octasaccharide corresponding to the following ABC-DEFGH sequence:

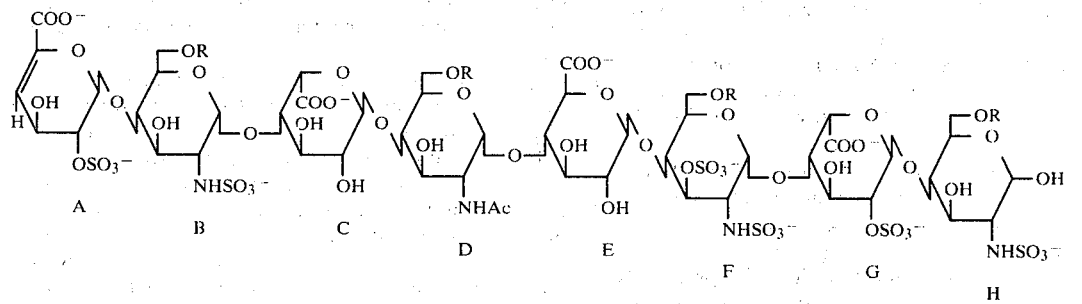

In the above formula R represents an hydrogen atom or a sulfate $(SO_3^-)$ group.

Another octasaccharide has ABGHCDEF sequence.

Active hexasaccharides of the invention also include moieties among said A,B,C,D,E,F,G and H moieties. One of these species has ABCDEF sequence.

Another species has CDEFGH sequence wherein C is an unsaturated uronic acid.

Another species is constituted by CDEFGH sequence (but where C is an iduronic acid residue).

Other active oligosaccharides are pentasaccharides, more particularly the one having DEFGH structure.

Shorter oligosaccharidic chains still biologically active are part of the present invention.

The pharmaceutically acceptable salts of said oligosaccharides are part of the invention as well.

The invention also aims at providing a process for obtaining fractions such as above disclosed, comprising heparin depolymerization and the treatment of the resulting depolymerization mixture so as to separate the fractions containing oligosaccharides having no more than 8 saccharidic moieties (advantageously the oligosaccharides per se) having a high AT III affinity and a high anti-Xa (Yin-Wessler) activity.

The depolymerization step is carried out under mild conditions so that the oligosaccharidic chains are not completely degradated and the moieties which are responsible (to a large extent) for anti-Xa (Yin-Wessler) activity are maintained.

Preferably, the depolymerizing conditions of the process defined hereabove are so adjusted as to maintain the capability of at least a part of the resulting oligosaccharides of being specifically retained on immobilized antithrombin III.

The above adjustment can also advantageously be based on the upkeeping of the capability of at least part of the resulting oligosaccharides to exhibit anti-Xa activity as measurable by the Yin-Wessler test, while having practically no more anticoagulant activity as measured by the USP test.

It will be appreciated that the threshold with respect to the adjustment of the depolymerization conditions need not necessarily be attained. It is nevertheless desirable to do so when high yields of oligosaccharides having Yin-Wessler anti-Xa activity are desired.

When depolymerizing heparin with $HNO_2$, it seems advantageous to carry out the reaction in aqueous medium, at a pH ranging from 2 to 4, preferably 3 and at a temperature close to ambient.

When depolymerizing with heparinase, a highly purified heparinase should preferably be used, in particular a bacterial heparinase, more especially originating from Flavobacterium heparinum. The conditions are controlled in order to obtain the smallest fragments still having an affinity for AT III and an anti-Xa (Yin-Wessler) activity.

It is advantageously carried out at a pH ranging from 6 to 8, in particular close to neutral and at a temperature close to ambient. The heparinase is gradually added in the reaction mixture until hydrolysis is over.

The depolymerization with the heparinase may optionally be carried out on the fractions resulting from the oligosaccharidic fractions obtained after degradation of heparin with $HNO_2$, or also on the oligosaccharides of higher molecular weight which are retained on immobilized AT III together with the active oligosaccharides having less than 8 moieties and which are then eluted with these oligosaccharides having shorter chains.

The separation and the recovery of the fractions which contain the desired oligosaccharides is advantageously carried out by affinity chromatography in a column contaning bound AT III.

Satisfactory results are obtained by using a gel of agarose such as the one commercialized under the trademark Sepharose, with ATIII molecules linked thereon.

To achieve the desired separation of the major part of the products contained in the depolymerization mixture and having a high anti-Xa activity, the column is advantageously equilibrated with a buffer having an ionic strength of about 0.2 M, preferably not less than 0.1 M, at a pH of 6 to 8, preferably close to or slightly higher than neutral.

The products devoid of or having a low affinity for AT III are eliminated by rinsing with a buffer advantageously of the same type as the one used for equilibrating the column.

A preferred embodiment for recovering the AT III retained or adsorbed products, having an anti-Xa activity (Yin-Wessler) comprises desorbing and recovering all of the oligosaccharides by eluting them with a buffer having a sufficient ionic strength to that effect. The buffer used for the above mentioned elution is further advantageously selected among those which do not interfere with the subsequent recovery steps (particularly with alcohol precipitation) of the oligosaccharides contained in the recovered fractions. A buffer containing a calcium salt, such as calcium chloride that remains soluble in presence of an alcohol concentration (any suitable alcohol, for instance ethanol) which causes the precipitation of the oligosaccharides, is thus preferred.

A sodium salt can also be used.

After elution of the products having an AT III affinity, an alcoholic precipitation is advantageously carried out to recover them, their separation being then made for example by centrifugation.

In order to have oligosaccharidic fractions having the required high anti-Xa activity (Yin-Wessler) and a satisfactory homogeneity, the mixture of all the oligosaccharides previously retained on AT III is fractionated by a gel filtration or by ion exchange chromatography or both or by any other method which would yield similar results.

Advantageously, the last mentioned fractionation is so monitored that after the larger molecules have been eluted, the smaller ones are recovered, starting from those fractions which have a Yin-Wessler titer and a USP titer which are in a ratio of at least 30, preferably 100, the recovery extending to all the remaining fractions which still exhibit anti-Xa activity at least in the Yin-Wessler test.

Depending upon the amounts of solution subjected to gel filtration or chromatography, the volume of the successively eluted fractions will be selected as a matter of routine in order to select the most appropriate fractions with respect to the desired application.

Alternatively before the step of fixation on AT III, the oligosaccharides having more than 8 saccharidic moieties are eliminated from the depolymerization mixture, advantageously by gel filtration or a similar process as indicated above.

Biologically active octa-, hepta-, hexa-, penta-, tetra- and trisaccharides can be isolated from the eluted fractions obtained.

The pharmacological study of the fractions and oligosaccharides of the invention has shown a relationship between their anti-Xa activity as expressed in Yin-Wessler units and their antithrombotic activity.

Said fractions and oligosaccharides appear then capable of exerting a strong antithrombotic activity. Due to their low or nil global anticoagulant activity, the risks of hemorrhages are advantageously practically eliminated.

Among the assays made in vivo in order to study their antithrombotic activity, the following test has been carried out on the rabbit.

The formation of thrombus has been caused in the jugular vein of the rabbit by injecting a complex of activated prothrombin.

The ability of ABCDEFGH octasaccharide having a Yin-Wessler titer of 2000 units/mg to avoid the formation of the thrombus has been studied by injecting the octasaccharide before the injection of 25 units/kg of thrombogenic complex.

When injecting the oligosaccharides before the thromboplastin complex at doses of 150 to 250 iu/mg Yin-Wessler, a significant fraction is obtained with respect to the formation of the thrombus.

Said octasaccharide appears then to have a strong antithrombotic activity. Advantageously, global anticoagulant activity is not detectable.

The oligosaccharide fractions according to the invention are free of toxicity. The administration of 10,000 U/kg (Yin-Wessler titer) of any of the fractions according to the invention causes in the rabbit neither any toxic reaction nor any pyrogenic effect in the pyrogenicity test in the rabbit according to the French Pharmacopea.

The compositions according to the invention are then particularly suitable for controlling specifically some steps of the coagulation in man or animal, more particularly when selective control of the activity of the blood factor Xa is desired (by way of example only, in patients, who are to undergo or who underwent surgery, in atheromatous diseases, perturbations of the coagulation mechanisms by bacterial or enzymatic activators, etc.).

The invention relates then to pharmaceutical preparations which contain oligosaccharidic fractions or the oligosaccharides themselves with high anti-Xa activity.

It relates more particularly to pharmaceutical preparation devoid of pyrogenic substances, containing an effective amount of active principles, in association with pharmaceutical excipients.

Particularly it concerns the compositions in which the pharmaceutical vehicle is suitable for the administration by oral route. Dosage forms of the invention suitable for the administration by oral route can advantageously be gastroresistant capsules, or tablets or pills.

Other pharmaceutical compositions include oligosaccharides or oligosaccharidic fractions in association with excipients suitable for the administration by rectal route. Corresponding dosage forms are suppositories.

Other dosage forms of the invention are sprays or ointments.

The invention also concerns pharmaceutical compositions which are injectable, sterile or sterilizable.

Such solutions advantageously contain 1,000 to to 100,000 U (Yin-Wessler)ml of the oligosaccharidic fraction, preferably from 5,000 to 50,000 for example 25,000 U/ml, when these solutions are intended for subcutaneous injection or containing again, for example, from 500 to 10,000 for example, 5,000 units/ml of the oligosaccharidic fraction or oligosaccharide when they are intended for intravenous injection or for perfusion.

Advantageously, these pharmaceutical preparations are presented in the form of non-reusable syringes, ready for use at any suitable time.

The invention also concerns pharmaceutical compositions containing said oligosaccharides in association with another active principle, in particular useful for the prophylaxis and the treatment of thrombosis such as a veinotonic agent like dihydroergotamine, a salt of nicotinic acid or a thrombolytic agent like urokinase.

The oligosaccharidic fractions and oligosaccharides of the invention are advantageously in the form of a salt of at least one physiologically acceptable metal, such as sodium and/or calcium and/or magnesium.

The pharmaceutical compositions according to the invention are particularly adapted to the control (preventive or curative) of the blood coagulation in man or animal, notably in those cases where the host is subjected to risks of hypercoagulability, more particularly those resulting from the release by the organism of thromboplastin, for example, of tissular thromboplastin (surgical operations, atheromatous processes, tumor development, disturbances of the coagulation mechanisms by bacterial or enzymatic activators, etc.). For the sole purpose of illustrating the invention, and without being a cause for limiting the protection of the invention, there will be indicated below, by way of example, a posology capable of being used in man: it comprises for example, the administration to the patient of 1,000 to 25,000 U by the sub-cutaneous route, 2 to 3 times daily, according to the level of hypercoagulation risk or the thrombotic condition of the patient, or from 1,000 to 25,000 U per 24 hours by the intravenous route, in discontinuous administration at regular intervals or continuously by perfusion, or again from 1,000 to 25,000 U (three times weekly) by the intramuscular route (titers expressed in Yin-Wessler U). The doses should naturally, be adjusted in each patient according to the results of previously effected blood analyses, the nature of the disorder from which the patient is suffering and, generally, his state of health, as is well known.

The invention also relates to the application of the oligosaccharides according to the invention for the preparation of a biological reactant usable in the laboratory, notably as a comparison reference for the study of other substances of which the anticoagulant activity is to be tested, notably at the level of inhibition of the factor Xa.

The description hereafter of examples of production of the oligosaccharides having YIN and WESSLER anticoagulant activity according to the invention will be given for the sake of further illustrating, yet in a non-limitative manner, the invention.

EXAMPLE 1

Method for obtaining oligosaccharidic fractions including the steps of:

I—depolymerizing heparin with $HNO_2$,

II—separating the biologically active oligosaccharides by chromatography on Sepharose -AT III, III—gel filtration of the eluted fractions and recovery of the desired products.

I. Depolymerization of heparin in the presence of nitrous acid 20 g of heparin (USP titer: 150 UI/mg, YIN-WESSLER titer: 150 U/mg) were dissolved in 800 ml of water at room temperature. 200 ml of 0.5 M sulfuric acid and then 13.8 g of sodium nitrite were then added (final molarities of sulfuric acid: 0.1 M, and of the nitrite: 0.2 M). A reaction accompanied by the release of gaseous nitrogen was then produced. The reaction was stopped 15 minutes later by adjusting the pH at 7–7.2 with 5 N sodium hydroxide. The depolymerization products were precipitated by ethanol (7 volumes) that is, in this case, 7 liters. The precipitate was centrifuged, washed with alcohol and dried under vacuum.

| Weight | 24.8 g |
|---|---|
| USP titer | nil |
| YIN-WESSLER titer | 7 U/mg |

The apparent increase of weight of the precipitate was due to partial precipitation of sodium sulfate together with the depolymerization products.

II. Chromatography on SEPHAROSE-antithrombin III

The latter depolymerization products were then submitted to a chromatography on a SEPHAROSE gel comprising antithrombin III retained thereon. A column (diameter 2.6 cm, height 40 cm) containing 200 ml of SEPHAROSE-AT III (approximately 10 mg of immobilized bovin antithrombin III per ml of SEPHAROSE) was equilibrated with a buffer consisting of NaCl 0.2 M. tris-HCl 0.05 M pH 7.2.

1.6 g of the abovesaid depolymerization products were dissolved in 16 ml of 0.2 M NaCl buffer and percolated through a column at a flow-rate of 50 ml/h and the column was rinsed by 500 ml of 0.2 M NaCl buffer.

The retained oligosaccharides were then eluted from the column by a buffer capable of desorbing all of the oligosaccharides retained on the immobilized antithrombin III ($CaCl_2$ 0.2 M, tris-HCl 0.05 M, pH 7.2). The part of effluent which contained the oligosaccharides was recovered and the said oligosaccharides were precipitated by 10 volumes of ethanol.

After washing with ethanol and drying under vacuum, 5 mg of products are recovered having a USP titer of 66 UI/mg and a YIN and WESSLER titer of 1,600 U/mg.

The products so obtained consisted of a mixture of mucopolysaccharides of high molecular weight and of oligosaccharides of low molecular weight.

III. Gel filtration 90 mg of a mixture of mucopolysaccharides and oligosaccharides obtained by a procedure of which the two preceding paragraphs are representative were dissolved in 2 ml distilled water, then deposited on the top of a column of the filtration gel formed of extremely fine particles commercialized under the denomination SEPHADEX G 50 (height 1 m, diameter 2.6 cm), equilibrated with distilled water. Development of the column with distilled water was carried out under a flow-rate of 24 ml/h. The effluent was recovered fraction-wise (6 ml per tube). The mucopolysaccharide content of each tube was evaluated by UV absorption at 206 nanometers.

The contents of the tubes were pooled to form the fractions numbered 1 to 5.

The mucopolysaccharides contained in each of these fractions were precipitated by alcohol and dried.

The weights and anticoagulant properties of these fractions were as follows:

| fraction (1) | weight: | 15 mg |
|---|---|---|
| | USP titer: | 156 UI/mg |
| | YIN-WESSLER titer: | 190 U/mg |
| fraction (2) | weight: | 16 mg |
| | USP titer: | 139 UI/mg |
| | YIN-WESSLER titer: | 520 U/mg |
| fraction (3) | weight: | 17 mg |
| | USP titer: | 50.3 UI/mg |
| | YIN-WESSLER titer: | 1 390 U/mg |
| fraction (4) | weight: | 40 mg |
| | USP titer: | 7 UI/mg |
| | YIN-WESSLER titer: | 870 U/mg |
| fraction (5) | weight: | 1 mg |
| | USP titer: | nil |
| | YIN-WESSLER titer: | 150 U/mg |

The ranges of molecular weights of the fractions so obtained, more particularly of the abovesaid "fraction 4" and "fraction 5" were appreciated both by paper chromatography and High Pressure Liquid Chromatography (HPLC) and on a comparative basis with the results obtained in the same experimental systems with a decasaccharide of heparin and:

in paper chromatography, with the reference products disclosed in the article of Silva and Dietrich (Silva M. E. et Dietrich C. P., J. Biol. Chem. Vol. 250 (1975) pp. 6, 841–6,846; and in HPLC on a silica gel, with a series of polystyrene-sodium sulfonates of increasing known molecular weights and heparin samples of known molecular weights.

"Fraction 4" was found to consist of an oligosaccharide having less than 8 saccharide units and most likely not more than 6 saccharide units, and "fraction 5" of an oligosaccharide having less than 6 saccharides, most likely not more than 4 saccharide units.

EXAMPLE 2

Method for obtaining oligosaccharidic fractions including the steps of:

A—depolymerizing heparin by digestion with an heparinase;

B—fractionnating the depolymerization mixture by gel filtration on DEAE Sephadex A 25;

C—selecting the biologically active products by chromatography on agarose AT III.

A—Depolymerizing heparin by digestion with an heparinase

1—Preparation of the heparinase:

Flavobacterium heparinum enzymes were used for degradating heparin.

The enzymes of flavobacterium heparinum were cultivated according to the method of Payza and Korn in J. Biol. Chem. 1956, 223, p. 853–858. The lyophilized cells were crushed under dry conditions in the presence of alumine and extracted by an acetate buffer at neutral pH.

The insoluble parts were eliminated and the solution was successively chromatographied on diethylaminoethyl cellulose and then on two agaroses such as those commercialized under the trademarks CM Sepharose CL 6B and Ultrogel ACA 54 respectively.

20 mg of heparinase having a degree of purity of 90% (the purity having been evaluated by electrophoresis) and a titer of 30,000 units/mg (8,333 units as measured by the method of Hovingh et al. (1970), J. Biol. Chem. 245 6, 1970) were thus obtained.

2—Depolymerization of heparin 1 g of heparin for use in therapy was dissolved in 50 ml of distilled water. 1 g of sodium acetate and 100 mg of calcium chloride were added thereto. The pH was adjusted to 7.2 by ClHO.1 N.

1 mg of a solution of highly purified bacterial heparinase having a titre of 30,000 units/mg (8,333 units as measured by the method of Hoving et al. (1970), J. Biol. Chem. 245, 6, 170) was added and the mixture was incubated for 15 hours at 30° C. After precipitation by 10 volumes of ethanol at 100° GL the depolymerized product obtained was dried. The product obtained was designated as P.

B—Fractionation on "DEAE SEPHADEX A 25"

A column having a 16 mm diameter containing 50 ml of the gel known under the above commercial designation was equilibrated with a 0.1 M NaCl, pH 7.0 buffer. 20 ml of a solution of 180 mg of the above product P in said buffer were deposited on the top of the column and eluted with a gradient formed starting from 250 ml of a 0.1 M NaCl, pH 7.0 buffer, on the one hand, and of a 0.5 M CaCl$_2$ pH 7.0 buffer, on the other hand. The flow rate was adjusted to 30 ml per hour. Successive 10 ml volumes were recovered.

The elution diagram (followed by optical density measurements at 232 nm) is represented on FIG. 1. The volumes were pooled into fractions 1, 2, 3, 4 according to the optical density measurements, as shown in FIG. 1. Their respective optical densities are shown in table 1 hereinafter.

TABLE I

| No. fraction | Weight | Yield in weight % from 120,8 mg of starting product | $[\alpha]_D^h$(c = 1, water) On the D band of sodium | DO.$^{232\,nm}_{H_2O}$ (conc: 1 mg/ml) |
|---|---|---|---|---|
| 1 | 22 mg | 18% | +33° | 2.1 |
| 2 | 69 mg | 57% | +30° | 3.2 |
| 3 | 20 mg | 16% | +30° | 2.6 |
| 4 | 9.8 mg | 8% | +21° | 1.7 |

C—Affinity chromatography on agarose AT III of the above second fraction

A column having a diameter of 2.5 cm containing 50 ml of agarose having AT III immobilized thereon (Agarose AT III) was equilibrated with 0.1 M. NaCl tris-HCl 0.025 M; pH 7.4.

60 mg of the fraction numbered 2 in table I (P 2) dissolved in 6 ml of the above buffer were deposited on the top of the column. Elution was carried out with successive solutions.

The first eluant used was the same as above: an effluent containing 50 mg of a product referred to as P 2 (B) contained in the first detected peak of optical density at 232 nm was separated therewith.

On changing the eluant to 0.2 M NaCl, 0.05 M tris HCl; pH 7.4, no active fraction was desorbed from the gel.

On further changing the eluant to 2 M CaCl$_2$ a peak was obtained. The volumes containing the fractions which gave rise to said peak were precipitated by alcohol to provide 5 mg of a highly active fraction according to the invention (referred to as P 2(A)).

The biological and physical characteristics of the last mentioned fraction are indicated herebelow:

YIN-WESSLER titer: 1,400 units/mg $[\alpha]_D^{20} = +24°$ (c=1, water)

DO.$_{HCl\,0.03}\,N^{235\,nm} = 4.5$

The analytical results concerning P 2 (A) fraction are as follows:

1—Chemical analysis

The components of P 2 (A) were dosed as concerned: the uronic acids, according to the method of Bitter T. et al. Anal. Biochem., 4, (1962), 330–334;

the hexosamines, on the one hand by the Elson-Morgan method, as modified by Antonopoulos C. A. et al., Biochem. Biophys. Acta 83, (1964), 1–19 (after hydrolysis of P 2 (A) by 6 N HCl for 4 hours, at 110° C. in a nitrogen atmosphere) and, on the other hand, by the method of Smith R. L. and Gilkerson E., Anal. Biochem., 98, (1979), 478–480, on samples of either non-hydrolysed or hydrolysed samples of P 2 (A);

the sulfates, by the method of T. T. Terho et al., Anal. Biochem., 41, (1971), 471–476.

The results as to composition are summed up in table II hereafter, expressed as weight % (first line), as the mole to mole ratio with respect to the glucosamine units after hydrolysis (H+) according to the technique of Smith and Gilkerson (second line).

TABLE II

|  | Uronic acids | Hexosamines Smith-Gil. H(+) | Antonopoulos | Sulfates |
|---|---|---|---|---|
| P 2 (A) | 15,2% | 18,7% | 12,8% | 12% |
|  | 0,9 | 1,0 | 0,7 | 1,4 |

The results show that the oligosaccharides of the invention comprise substantially:

1 mole of uronic acid per 1 mole of hexosamine;

1.4 mole of sulfate per disaccharidic unit (including an uronic unit and an hexosamine unit);

2 N-sulfate-glusosamine units, per 1 N-acetylglusocamine units.

2—High Pressure Liquid Chromatography

50 μl of a solution of 0.5 mg/ml of P 2 (A) were subjected to an elution by 0.02 M $Na_2SO_4$ (1 ml/minute) through a series of a first and second columns (250×4.6 cm) respectively filled with silica commercialized under the designation LICHROPHOSPHER Si 100, and a third column (250×3 cm) of the material commercialized (by Waters and Associates) under the designation microBONDAGEL. The molecular weight of the fraction according to the invention was approximated by its time of elution (or of retention on the columns) with reference to the linear variations of the retention times of standard polystyrene-sulfonates of known molecular weights (of respectively 4,000, 6,500, 16,000 and 31,000) as well as of a tetrasaccharide having a known molecular weight of 700–900 subjected to the same assays, as a function of the logarithm values corresponding to said molecular weights. The measurements were made using a SPECTRAPHYSICS 3500 chromatograph, and the detection of the fraction by UV spectrophotometry (200 mμ and 230 mμ).

This assay, as well as an other chemical assay according to the method A. Linker and P. Hovingh, Biochem. Vol. 11, No. 4, 1972, p. 563–567, confirmed the fact that the active oligosaccharide contains not more, and even less than 8 saccharidic units.

3—Ultra-violet absorption

UV-absorption was carried out on a solution of 100 γ/ml of P 2 (A) and in an UV band of 215–260 nm. Maximum absorption was observed in the 230–235 nm band.

EXAMPLE 3

Method for obtaining oligosaccharidic fractions including the steps of:

I—enzymatic depolymerization of heparin;
II—selecting the biologically active products by chromatography on Sepharose AT III;
III—gel filtration of the eluted fractions and recovery of the desired products.

I—Enzymatic depolymerization of heparin 20 mg of heparin for use in therapy were dissolved in 100 ml of an acetate buffer (NaOAc 0.15 M, NaCl 0.15 M; Ca $Cl_2$ 0.005 M; pH 6.9).

The solution was incubated for 24 hours at 30° C.

The highly purified heparinase previously obtained was added to the solution as follows:

0.4 mg (amount based on the dosage of the proteins) at the time t=0,
0.2 mg at the time t= +8 hours,
0.2 mg at the time t= +24 hours At t= +36 hours, another addition of heparinase did not cause an increase of the optical density at 232 nm. The reaction was considered as ended and the products were recovered by alcoholic precipitation and were dried (yield in weight 90%).

II—Affinity chromatography on Sepharose AT III of the depolymerized products A chromatography column (5×18 cm) containing 10 mg of bound AT III/ml of Sepharose was equilibrated with 0.1. M Na Cl; tris-HCl 0.05 M; pH 7.5.

2 g of the products of degradation of heparin were deposited on the top of the column.

The column was rinsed with said buffer whereby the unfixed fractions were eliminated (the corresponding products being designated as UP hereinafter).

The fixed products (designated as FP- were then eluted with a solution of $CaCl_2$ 1 M pH 7.2.

The products were precipitated with alcohol and recovered by centrifugation. 1.6 g UP on the one hand and 8 mg of FP having 800 ui/mg (Yin-Wessler), on the other hand are thus recovered.

III—Gel filtration

UP and FP products were subjected separately to gel filtration 25 mg of each product were filtrated on a column (200×0.6 cm) of a Sephadex G 50 Superfine gel.

Figure 3:
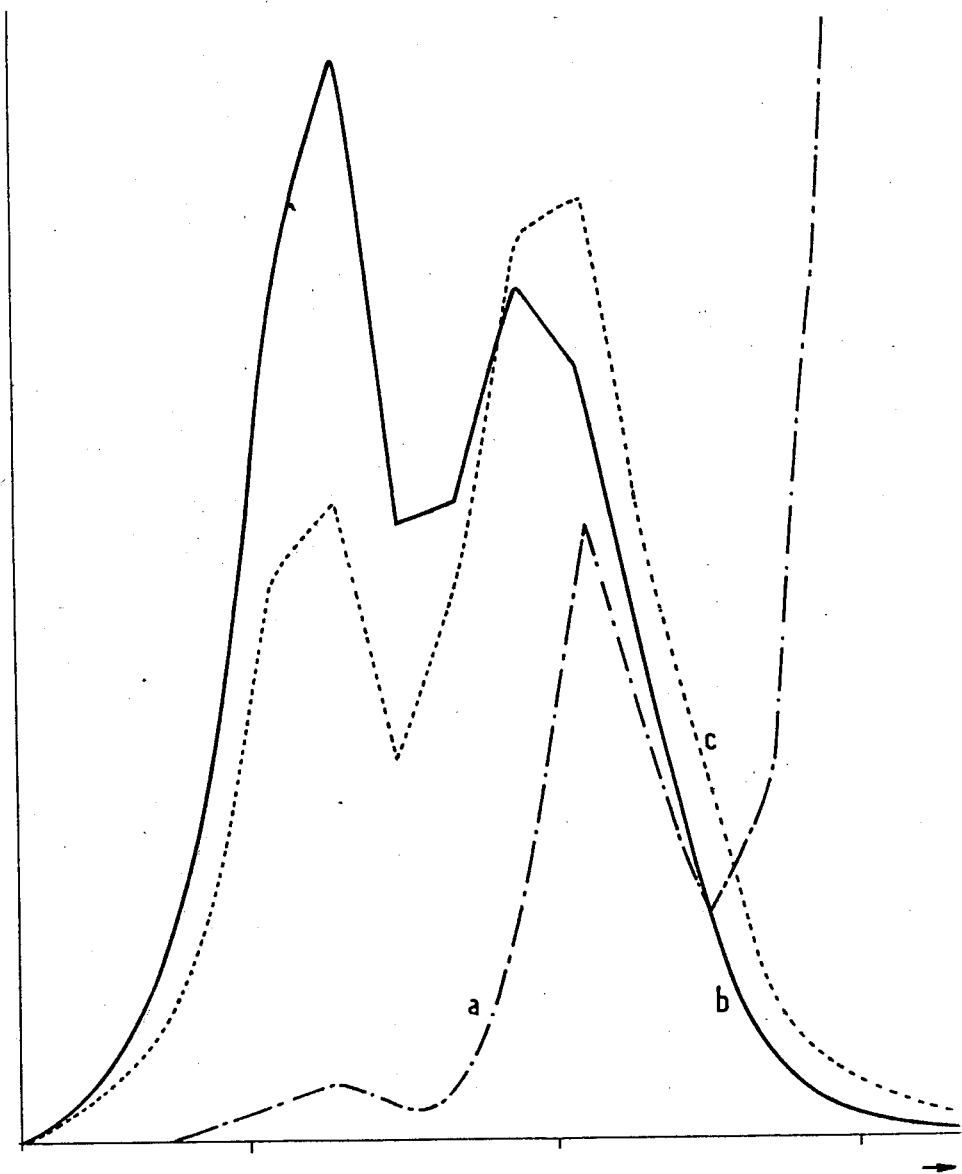

The elution was carried out using a solution of NaCl 0.2 M. Fractions of 0.65 ml were collected. After elimination of the salts on Sephadex G 25, the products were lyophilized, FIG. 3 represents the elution diagrams of UP fractions (continuous line) and FP (fractions (dotted line). The elution has been controlled by optical density measurements at 230 nm (absorption wavelength of the double bond created by the heparinase).

Figure 2:
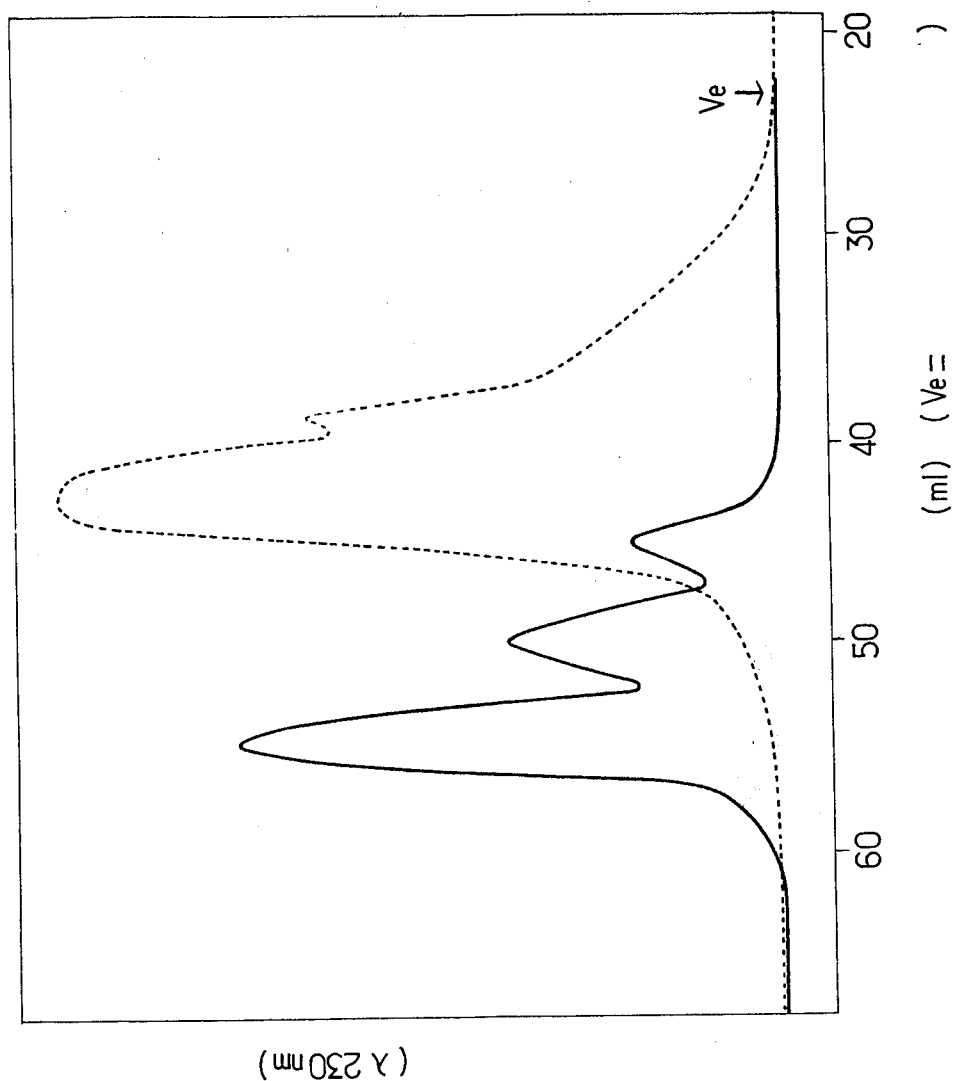

According to the optical density measurements, UP fraction was fractionated into di-, tetra-, hexa- and octasaccharides ($UP_2$, $UP_4$, $UP_6$ and $UP_8$) and into another product having a higher polymerization degree ($UP_{+8}$). $UP_8$ and $UP_{+8}$ do not appear on the elution curve of FIG. 2 as they only represent a very low percentage (3.4 and 1.3% respectively) and are only detected at high sensitivity.

FP fraction was separated into four fractions designated $FP_a$,b,c, and d, according to the order of the decreasing elution volume. The major part of FP fractions is eluted slightly before UP fraction.

Results concerning each of UP and FP fractions are given in the table hereinafter.

They comprise: the elution volume (ml) of each of said fractions, issued from UP and FP fractions; the % of each of them in the mixture of the UP and FP fractions respectively, the specific rotatory power of each fraction (measured with an electronic polarimeter in aqueous solutions usually 1%); the absorbance at 230 mn (measured in a 0.01% solution in HCl 0.03 M, the results being expressed as optical density of 1%°/$_{oo}$ solution); and the anti-Xa activity in human plasma of FP fractions measured according to the test of Yin and Wessler above mentioned.

TABLE

| Fraction | Elution Volume (ml) | % in the mixture | $[\alpha]_D^{20}$ (c = 1, water) on the D band of sodium | DO.$\frac{230\,nm}{H_2O}$ | Activity anti-Xa ui/mg Yin-Wessler |
|---|---|---|---|---|---|
| UP 2 | 52–60 | 52 | +5 | 6 | — |
| UP 4 | 47–52 | 30,5 | +23,5 | 4,8 | — |
| UP 6 | 43–47 | 13 | +37 | 3,3 | — |
| UP 8 | 40–43 | 3,4 | +41,5 | 2,5 | — |
| UP +8 | 37–40 | 1,3 | | 2 | — |
| FPa | 40–45 | 50 | +39 | 3,2 | 1200(2000 in another te) |
| FPb | 35–39 | 23 | +41 | 2,5 | 930 |
| FPc | 27–34 | 14 | — | — | 200 |
| FPd | 23–26 | 5 | — | — | 330 |

It appears from the results given in the table that each of the FPa fractions exhibit an anticoagulant activity, FPA having the most important biological activity. It will be noted that it represents 50 to 75% of the FP mixture. The FPa fraction was submitted to various treatments in order to elucidate its structure. The following analytical results were obtained.

Degradation of FPa by treatment with nitrous acid

The FPa fractions recovered after the gel filtration were incubated with $HNO_2$ in an aqueous medium under conditions enabling degradation of the oligosaccharidic chains. The degradation was carried out according to the method of Shiveley and Conrad in Biochemistry 1976, 15, p. 3932–3942.

Under the action of $HNO_2$ the oligosaccharidic chains are fragmented into di- and tetrasaccharides, the break taking place behind the N-sulfated glucosamine moieties said moieties being converted into 2,5 anhydromannose groups.

The di- and tetrasaccharides so obtained are separated by chromatography on Sephadex G50 (200×0.5 cm; NaCl 0.2 M.)

The elution diagram is given on FIG. 3.

The following measurements are made on each fraction: the optical density at 230 nm (curve a) the amount of uronic acids (curve b) of 2,5-anhydro-mannose (curve c) and of glucosamine (before and after acid hydrolysis), the radioactivity when the analysed products have been tritiated before being degradated by $HNO_2$.

The optical density measurement of these fractions shows that the major part of the unsaturated molecules are disaccharides, 90% of the optical density being in the peak of the disaccharide while 10% are in the peak of the tetrasaccharidic fragment.

It can be considered therefrom that the tetrasaccharidic unit does not contain an uronic acid moiety with a double bond. Such moiety is part of a disaccharide which contains further an N-sulfoglucosamine, this disaccharide GH is located at the non reducing end of the oligosaccharide before its nitrous degradation.

Besides, by dosing 2,5 anhydro-mannose groups in these fractions (curve c in FIG. 3), 33% of 2,5 anhydromannose groups are found in the tetrasaccharidic fragments and 66% in the disaccharide fragments. By assuming that the oligosaccharidic chains are N-sulfoglucosamine terminated, it can be concluded from said results that FPa contains two disaccharidic chains for one tetrasaccharidic chain (see curve b on FIG. 3). Said results were confirmed by the dosage of the uronic acids (curve b) according to Bitter and Muir in Annal; Biochem. 1962,4 p 330–334 and of the glucosamine moieties in the degradated products originating from FPA, i.e. said degradated products comprise twice as many disaccharidic molecules as tetrasaccharidic molecules.

Reduction of fraction FPa by sodium borohydride followed by nitrous degradation

By reducing FPa before the nitrous degradation, the reducing ends of the chains are not converted into 2,5-anhydro-mannose during the nitrous degradation. The reduction is carried out with a sodium borohydride buffer at pH 9.5. The reducing ends of the FPa oligosaccharidic chains are then converted into tritiated hexitols. The reduced product is separated from the salts present in the mixture by filtration on Sephadex G 25. It is then submitted to nitrous acid degradation and gel filtration as described above. The dosage of 2,5-anhydromannose groups is then carried out and shows a clear decrease of said groups in the disaccharidic fraction while the tetrasaccharidic fractions remain practically unchanged.

By reducing with tritiated borohydride, 70 to 80% of the radioactivity are found in the disaccharides and 20 to 30% in the tetrasaccharides. Furthermore, it was observed that after said treatment, the amount of 2,5-anhydromannose decreases far more in the disaccharidic peak than in the tetrasaccharidic peak—such result being in favour of the presence of a disaccharidic fragment at the reducing end (70% of the molecules) and also of a tetrasaccharide (30%).

Nitrous acid degradation of FPa fraction under very mild conditions

The FPa fraction was further submitted to a nitrous acid degradation under very mild conditions.

It was thus possible to obtain, after gel filtration and affinity chromatography can oligosaccharide fraction containing mainly the two hexasaccharides with ABCDEF and CDEFGH sequences the latest being also part of the invention.

The procedure involved treatment of the said FPa fraction with nitrous acid as described by Cifonelli and King (Carbohydrate Res. 1972, 21,pp. 173–186), except that the reaction was stopped between 1 and 5 mn and preferably 3 mn. The fragments thus obtained were desalted by gel filtration on Sephadex G 25 and submitted to an affinity chromatography in the same conditions as described above.

Two main species, i.e. CDEFGH and ABCDEF were found in the eluted fractions, as shown by the analytical methods described above for study of the FPa fraction. They still had a high anti-Xa activity (Yin and Wessler).

NMR characterization of an octasaccharidic fraction

The octasaccharidic fraction was isolated. It presented a YW titer of 2000 IU/mg and an APTT titer of 4 IU/mg.

The $^{13}C$ NMR spectrum of this product was recorded (see FIG. 5). It confirms that the product is an octasaccharide. It also confirms the assigned structure (ABCDEFGH sequence).

The signals observed are respectively characteristic of the:

anomeric carbon in position 1 (90-105 ppm) of the various moieties (A,B,C,D,E,F,G and H) of the structure (the corresponding moiety being mentioned for each peak to enable their identification);

carbons in position 6 on the figure (about 60 and about 70 ppm) (signal $C_6$) and in position 2(55-60 ppm) (signal $C_2$) of the moieties;

$CH_3$ of —NHAc group in D (about 25 ppm). Furthermore the presence of a new resonance signal in the C-2 region of N-sulfo-amino-glucosamine residue is observed (signal *) (this signal does not correspond to any resonance signal in NMR spectra obtained under similar conditions with a conventional heparin).

EXAMPLE 4

Isolation of an anti-factor Xa active hexasaccharide fraction

In another set of experiments, the mixture obtained after the affinity chromatography step (81 mg), was chromatographied on a column (200×2.5 cm) of Sephadex G-50 Superfine gel.

Figure 4:
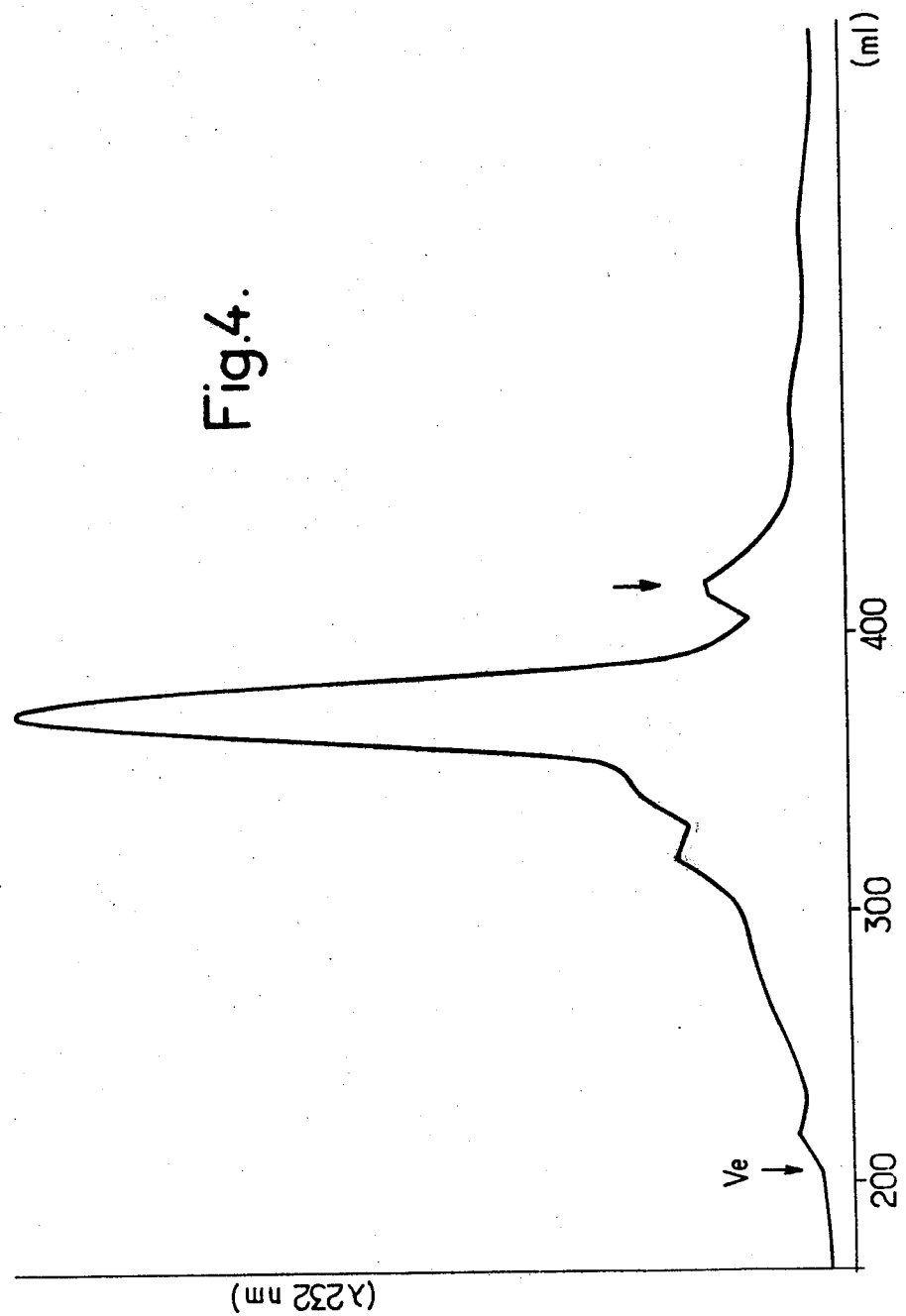

The elution was performed with 0.2 M sodium chloride. The products were detected by U.V. absorption at 232 nm (see FIG. 4).

The major part of the product was eluted in the octasaccharidic region, and presented the same properties as the product previously described.

The hexasaccharide fraction was collected and the salts were eliminated. The product thus obtained was freeze-dried. The yield was 2 mg.

This compound was highly active in the YW test: 510 IU/mg. Its APTT titer was 3IU/mg.

Since this hexasaccharidic fraction is obtained after heparinase degradation, it contains the residues A and H characterized in the octasaccharidic fraction. Moreover, since this product presents affinity for ATIII it should contain a CDEF tetrasaccharidic sequence. Thus it can be represented by ABCDEF structure.

However, one cannot exclude the presence, in this material, of small amount of a product having CDEFGH structure, where C is an unsaturated hexuronic acid residue (the 2-OH group being sulfated or not).

A study carried out as described for the octasaccharide (i.e. nitrous acid degradation and examination of the fragments) indicates the presence of both ABCDEF and CDEFGH.

EXAMPLE 5

Degradation of ABCDEFGH octasaccharide and oligosaccharides obtained

1—By using the method described by L. A. Fransson in Carbohydrate Research 62,235-244 1978 ABCDEFGH octasaccharide is submitted to an oxidation reaction with sodium periodate in phosphate medium, pH 7 at 37° C. during about 14 hours.

An alkaline hydrolysis is caused by adding NaOH to a pH of 11-12 and the reaction mixture is allowed to stay at room temperature for 30 minutes. It is then neutralized a trisaccharide which is likely to have a structure FGH is separated by chromatography on Sephadex G 50.

The determination of the anti-Xa activity according to the Yin-Wessler test give a value about 100-200 ui/mg depending on the assay.

2—Said octasaccharide is submitted to the action of a purified heparitinase, extracted from *Flavobacterium heparinum*. The experimental conditions (in particular, pH, temperature, time) correspond to those used in the enzymatic degradation according to example 2.

Two tetrasaccharides to which structures EFGH and ABCD can be given are recovered by filtration on SEPHADEX G 50 (carried out as in example 2).

By passing the tetrasaccharides through a column of Sepharose AT-III, EFGH is be retained while ABCD is eliminated. EFGH is then recovered by elution with a solution NaCl 1 M. The Yin-Wessler activity, measured in various assays, is about 100-200 ui/mg.

3—Octasaccharide ABCDEFGH is submitted to a mild nitrous degradation.

1 mg of octasaccharide is used per ml of solution—$HNO_2$ is generated in situ by adding $NaNO_2$ N/1000 and HCl.

The pH is adjusted to 3.

After 10 mn, at the ambient, the pH is adjusted to 7.

The reaction mixture is submitted to a gel filtration followed by an affinity chromatography, using the conditions disclosed in the preceeding examples. By eluting with NaCl 1 M or $CaCl_2$ 1 M, a product can be recovered having presumably hexasaccharidic structure CDEFGH.

Said product is submitted to the action of an iduronidase extracted from human kidney. The enzymatic degradation step is carried out at pH 7 at 37° C.

An oligosaccharide to which pentasaccharidic structure DEFGH is attributed is obtained by filtration of the depolymerization mixture on Sephadex G 50. The anti-Xa (Yin-Wessler) activity of this product appears to be over 400 ui/mg.

EXAMPLE 6

NMR characterization of the oligosaccharidic fraction obtained according to example 1

The $^{13}C$ NMR spectrum of this fraction shows the presence of said signal * in the region of C-2 of glucosamine residues (see FIG. 6). This signal can be assigned to a glucosamine unit which is N-sulfated and substituted by a $—OSO_3^-$ group in position 3.

This glucosamine unit is sulfated or not in position 6.

Furthermore, the integral curve confirms that the product has an average number of moieties of less than 8 and comprises a major part of hexasaccharidic and octasaccharidic species.

Starting from beef lung heparin, after controlled degradation, followed by affinity chromatography and gel filtration as described above an octasaccharide having the structure ABCFGHGH can be isolated. This product was highly active in an anti-Xa assay.

An hexasaccharide ABCFGH was also extracted in minute amount. It was also active in an anti-Xa assay.

The invention extends of course to the oligosaccharides that may be obtained by other depolymerization techniques of heparin or heparinic compounds followed by the subsequent recovery of the oligosaccharides of low molecular weight having anticoagulant activity as measurable by the YIN-WESSLER test.

As an example of another depolymerization technique of heparin or related compounds, one may cite periodic oxidation. One may also cite the technique which consists in producing an α,β elimination reaction by chemical means on heparin or esters of heparin giving similar results, or the process which comprises:

contacting the starting heparin fraction with antithrombin III immobilized on a Sepharose gel to fix the antithrombin-binding components of said heparin fraction, digesting the so fixed heparin with a bacterial heparinase and eluting the antithrombin-binding fragments from the gel whereby the eluant containing the above said fragments, all of which may then be subjected to the further steps of the above-defined process.

We claim:

1. A process for obtaining oligosaccharides and oligosaccharide fractions having activity against activated factor X of blood, as determined by the Yin-Wessler titer, (anti-Xa activity) comprising the steps of:

contacting heparin or a heparin fraction possessing anticoagulant activity and comprised of polysaccharide chains of molecular weight ranging from about 2,000 to about 50,000, with an agent capable of depolymerizing or fragmenting the heparin polysaccharide chains, under conditions adjusted to obtain a mixture which contains an oligosaccharide fraction of reduced molecular weight composed of fragments or chains constituted by no more than 8 saccharide moieties having said anti-Xa activity and including a sequence of less than 8 saccharide moieties, which sequence has binding affinity for AT III (antithrombin III) and is responsible for the specific anti-Xa activity of said oligosaccharide fraction, separating at least the major part of said oligosaccharide fraction by (a) contacting the mixture with AT III to retain at least the major part of said oligosaccharide fraction having said anti-Xa activity and the binding affinity for AT III, (b) eliminating from the mixture the material not retained by AT III and (c) separating said oligosaccharide fraction from said AT III.

2. A process according to claim 1 wherein heparin is depolymerized by a chemical process which splits the heparinic chains between an N-sulfate glucosamine unit and the following uronic acid unit.

3. A process according to claim 2 wherein heparin is depolymerized with nitrous acid.

4. A process according to claim 3 wherein the heparin is depolymerized with nitrous acid in an aqueous medium at a pH of about 2 to 4 at about ambient temperature.

5. A process according to claim 1 wherein heparin is depolymerized by an enzymatic process which cleaves the heparinic chain between the anomeric carbon of an N-sulfate glucosamine residue and the following uronic acid unit.

6. A process according to claim 5 wherein heparin is depolymerized with bacterial heparinase at a pH of about 6 to 8 and at about ambient temperature.

7. A process according to claim 1 wherein heparin is depolymerized with purified bacterial heparinase originating from Flavobacterium heparinum.

8. A process according to claim 1, 2 or 5 wherein the separation of the major part of said oligosaccharide fraction from said mixture which contains an oligosaccharide of reduced molecular weight is carried out by affinity chromatography on a column containing bound AT III.

9. A process according to claim 8 wherein the column is equilibrated with a buffer having an ionic strength of about 0.1 M to about 0.2 M, and the separation is carried out on said column at a pH of 6 to 8, and wherein the components of the mixture having little or no affinity for AT III are eliminated by rinsing with a buffer solution.

10. A process according to claim 1, 2 or 5 and further comprising recovering the oligosaccharide fraction retained by said AT III by eluting said retained oligosaccharide fraction with a buffer having an ionic strength sufficient to separate said oligosaccharide fraction from said AT III, said buffer being selected among those which do not interfere with subsequent recovery steps including alcohol precipitation of the oligosaccharides contained in said fraction.

11. A process according to claim 1, 2 or 5 further comprising fractionating the mixture of oligosaccharides retained by said AT III.

12. The process according to claim 11 wherein said fractionation is carried out by gel permeation eluting first the larger molecules, then the smaller molecules are eluted and those fractions which have a Yin-Wessler titer and a USP titer which are in a ratio of at least 30 are recovered and the recovery is continued until all fractions which exhibit anti-Xa activity have been eluted and recovered.

13. The process of claim 12 wherein those fractons which have a Yin-Wessler titer and a USP titer in a ratio of at least 100 are recovered.

14. A process according to claim 1, 2 or 5 wherein before said mixture is contacted with AT III, separating the oligosaccharides having more than 8 saccharide moieties are from the mixture.

15. The process of claim 14 wherein oligosaccharides having more than 8 saccharide moieties are separated from the mixture by gel filtration.

* * * * *

UNITED STATES PATENT AND TRADEMARK OFFICE
CERTIFICATE OF CORRECTION

PATENT NO. : 4,401,758
DATED : August 30, 1983
INVENTOR(S) : Lormeau et al

It is certified that error appears in the above-indentified patent and that said Letters Patent is hereby corrected as shown below:

On the title page, Under Foreign Application Priority Data add:

--Nov. 6, 1978    [FR]    France ...................... 78 31357
  Jul. 20, 1979    [FR]    France ...................... 79 18873--

Signed and Sealed this

Twenty-ninth Day of March, 1994

Attest:

BRUCE LEHMAN

Attesting Officer     Commissioner of Patents and Trademarks